United States Patent
Funyuu et al.

(10) Patent No.: US 9,496,509 B2
(45) Date of Patent: *Nov. 15, 2016

(54) ORGANIC ELECTRONIC MATERIAL, INK COMPOSITION, AND ORGANIC ELECTRONIC ELEMENT

(71) Applicant: HITACHI CHEMICAL COMPANY, LTD., Tokyo (JP)

(72) Inventors: Shigeaki Funyuu, Tsuchiura (JP); Naoki Asano, Tsukuba (JP); Kenichi Ishitsuka, Tsukuba (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 50 days.

This patent is subject to a terminal disclaimer.

(21) Appl. No.: 14/361,803

(22) PCT Filed: Nov. 29, 2012

(86) PCT No.: PCT/JP2012/080861
§ 371 (c)(1),
(2) Date: May 30, 2014

(87) PCT Pub. No.: WO2013/081031
PCT Pub. Date: Jun. 6, 2013

(65) Prior Publication Data
US 2014/0335375 A1  Nov. 13, 2014

(30) Foreign Application Priority Data

Nov. 30, 2011 (JP) .................. 2011-262059

(51) Int. Cl.
*C09D 11/52* (2014.01)
*H01L 51/00* (2006.01)
*C08K 5/17* (2006.01)
*C08L 101/12* (2006.01)
*H05B 33/02* (2006.01)
*H05B 33/10* (2006.01)
*C07C 211/45* (2006.01)
(Continued)

(52) U.S. Cl.
CPC ......... *H01L 51/0077* (2013.01); *C07C 211/45* (2013.01); *C07C 211/48* (2013.01); *C08J 7/047* (2013.01); *C08K 5/17* (2013.01); *C08K 5/55* (2013.01); *C08L 101/12* (2013.01); *C09B 69/02* (2013.01); *C09D 11/52* (2013.01); *H01L 51/008* (2013.01); *H01L 51/0035* (2013.01); *H05B 33/02* (2013.01); *H05B 33/10* (2013.01); *C08J 2365/00* (2013.01); *H01L 51/0007* (2013.01); *H01L 51/5056* (2013.01); *H01L 51/5072* (2013.01); *H01L 51/5088* (2013.01)

(58) Field of Classification Search
CPC ......... C08K 5/17; C08K 5/55; C08L 101/12; H05B 33/02; H05B 33/10; C09D 11/52; H01L 51/008; H01L 51/0035; H01L 51/0077; C07C 211/45; C07C 211/48; C09B 69/02; C08J 7/047
USPC ............................................ 252/500, 301.16
See application file for complete search history.

(56) References Cited

U.S. PATENT DOCUMENTS 5,554,664 A     9/1996  Lamanna et al.
9,337,429 B2 *  5/2016  Funyuu ................ H01L 51/506
(Continued)

FOREIGN PATENT DOCUMENTS

CN  1177346 A     3/1998
EP  1725079 A1   11/2006
(Continued)

OTHER PUBLICATIONS

Notification of Transmittal of Copies of Translation of the International Preliminary Report on Patentability mailed Jun. 19, 2014, in connection with International Application No. PCT/JP2012/080861.
M. A. Baldo, et al., "High-efficiency fluorescent organic light-emitting devices using a phosphorescent sensitizer", *Nature*, vol. 403, Feb. 17, 2000, pp. 750-753. (Corrected).
(Continued)

*Primary Examiner* — Douglas Mc Ginty
(74) *Attorney, Agent, or Firm* — Fitch, Even, Tabin & Flannery LLP

(57) ABSTRACT

Provided is an organic electronic material which is excellent in curability at low temperatures in the case as an ink composition, and able to prepare an organic electronic element capable of reducing the driving voltage and of being driven stably for a long time. The organic electronic material is characterized by containing at least an ionic compound represented by the following general formula (1), and a compound including a charge transporting unit. [In the general formula (1), Ar represents an aryl group or a heteroaryl group, $R^a$ to $R^b$ each independently represent a hydrogen atom (H), an alkyl group, a benzyl group, an aryl group, or a heteroaryl group, and Ar, $R^a$ and $R^b$ may be linked to each other to form a ring. However, at least one of $R^a$ to $R^b$ is any of a hydrogen atom, an alkyl group, and a benzyl group. A represents an anion.]

General Formula (1)

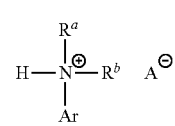

20 Claims, 1 Drawing Sheet

(51) Int. Cl.
*C07C 211/48* (2006.01)
*C09B 69/02* (2006.01)
*C08J 7/04* (2006.01)
*C08K 5/55* (2006.01)
*H01L 51/50* (2006.01)

(56) References Cited

U.S. PATENT DOCUMENTS

| | | | |
|---|---|---|---|
| 2005/0118381 A1* | 6/2005 | Kitayama | C07C 211/54 428/64.4 |
| 2009/0174311 A1 | 7/2009 | Patel et al. | |
| 2012/0074360 A1* | 3/2012 | Funyuu | H01L 51/0035 252/500 |
| 2012/0181530 A1 | 7/2012 | Funyuu et al. | |
| 2013/0037753 A1* | 2/2013 | Ishitsuka | H01B 1/122 252/500 |
| 2014/0332791 A1* | 11/2014 | Funyuu | H01L 51/506 257/40 |
| 2016/0218290 A1* | 7/2016 | Funyuu | H01L 51/506 |

FOREIGN PATENT DOCUMENTS

| | | |
|---|---|---|
| JP | 6-161131 | 6/1994 |
| JP | 6-161131 | 7/1994 |
| JP | 11-501909 | 2/1999 |
| JP | 2000-36390 | 2/2000 |
| JP | 2000-036390 A | 2/2000 |
| JP | 2006-133162 A | 5/2006 |
| JP | 2006-233162 | 9/2006 |
| JP | 2007-520858 | 7/2007 |
| TW | 201125888 A1 | 8/2011 |
| WO | 96/27584 A1 | 9/1996 |
| WO | WO 96/27584 A1 | 9/1996 |
| WO | WO 2005/059951 | 6/2005 |
| WO | WO 2005/59951 | 6/2005 |
| WO | WO 2008/010487 A1 | 1/2008 |
| WO | 2010/140553 A1 | 12/2010 |
| WO | 2011/040531 A1 | 4/2011 |
| WO | WO 2011/132702 | 10/2011 |
| WO | WO 2011/132702 A1 | 10/2011 |

OTHER PUBLICATIONS

Official Action issued on Feb. 3, 2015, in the counterpart Japanese Application No. 2013-547199.
Extended European Search Report mailed Sep. 11, 2015, for European Application No. 12854058.0; 6 pages.
M. A. Baldo, et al., "Highly efficient phosphorescent emission from organic electroluminescent devices", *Nature* vol. 395, Sep. 10, 1998, pp. 151-154.
M. A. Baldo, et al., "High-efficiency fluorescent organic light-emitting devices using a phosphorescent sensitizer", *Nature* vol. 408, Feb. 17, 2000, pp. 750-753.
C. Adachi, et al., "High-efficiency red electrophosphorescence devices", *Applied Physics Letters* vol. 78. No. 11, Mar. 12, 2001, pp. 1622-1624.
Office Action mailed Dec. 31, 2015, for Chinese Application No. 201280058823.9, together with English language translation thereof.
M. A. Baldo et al., Very high-efficiency green organic light-emitting devices based on electrophosphorescence, Applied Physics Letters, Jul. 5, 1999, pp. 4-6, vol. 75, No. 1.
Office Action mailed Nov. 19, 2015, for Korean Application No. 10-2014-7017665, together with English language translation thereof.
Office Action mailed Jul. 26, 2016, for Korean Application No. 10-2014-7017665, together with English language translation thereof.
Office Action mailed Jul. 22, 2016, for Taiwanese Application No. 101145146, together with English language translation thereof.

\* cited by examiner

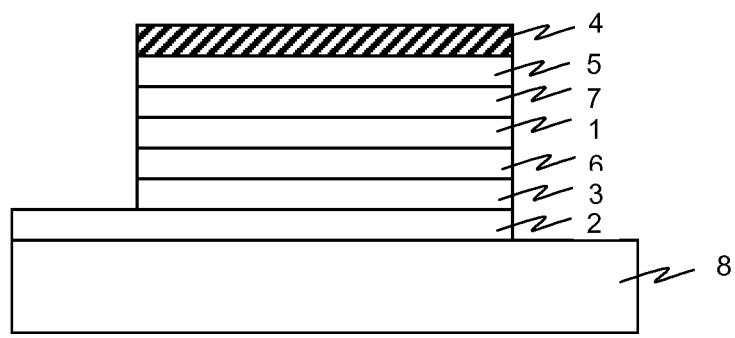

ORGANIC ELECTRONIC MATERIAL, INK COMPOSITION, AND ORGANIC ELECTRONIC ELEMENT

TECHNICAL FIELD

The present invention relates to an organic electronic material, an ink composition, an organic electronic element, and an organic electroluminescent element (hereinafter, also referred to as an organic EL element).

BACKGROUND ART

Organic electronic elements are elements intended for electrical operations with the use of organic matters, expected to be able to provide features such as energy conservation, low prices, and flexibility, and attracting attention as alternative techniques to conventional inorganic semiconductors mainly containing silicon.

Examples of the organic electronic elements include organic EL elements, organic photoelectric conversion elements, and organic transistors.

Among the organic electronic elements, the organic EL elements are attracting attention, for example, as alternatives to incandescent lamps and gas-filled lamps, and for use as large-area solid-state light sources. In addition, the organic EL elements are also attracting attention as most likely self-luminous displays in place of liquid crystal displays (LCD) in the field of flat panel display (FPD), and increasingly put into production.

In recent years, for the purpose of improving the organic EL elements in luminescent efficiency and lifetime, attempts have been made to use a charge transporting compound mixed with an electron-accepting compound.

For example, Patent Literature 1 discloses a composition composed of an ionic compound and a charge transporting compound, as a composition for charge transporting films.

For the purpose of improving the organic EL elements in luminescent efficiency and lifetime, attempts have been made to use a charge transporting compound mixed with an electron accepting compound.

For example, Patent Literature 1 discloses a composition composed of an ionic compound and a charge transporting compound, as a composition for charge transporting films.

As just described, it is considered important to produce a compound composed of radical cations of the charge transporting compound and counter anions, which is produced in the case of mixing the charge transporting compound and the electron accepting compound.

On the other hand, the organic EL elements are classified roughly into two types of: low molecular weight-type organic EL elements and high molecular weight-type organic EL elements, according to materials and film forming methods used. The high molecular weight-type organic EL element are essential elements to large-screen organic EL displays in the future, because organic materials are composed of high molecular weight materials, and able to be easily formed by printing, ink-jet printing, etc., as compared with the low molecular weight-type organic EL elements which require film formation in a vacuum system.

Both the low molecular weight-type organic EL elements and high molecular weight-type organic EL elements have been energetically researched, but still have the significant problem of being low in luminescent efficiency and short in element lifetime. As one means for solving this problem, multi-layered elements have been attempted for the low molecular weight-type organic EL elements.

FIG. 1 shows an example of a multi-layered organic EL element. In association with FIG. 1, a layer in charge of light emission is referred to as a light emitting layer 1, and in the case of including other layers, a layer in contact with an anode 2 is referred to as a hole injecting layer 3, and a layer in contact with a cathode 4 is referred to as an electron injecting layer 5. Furthermore, when there is a distinct layer between the light emitting layer 1 and the hole injecting layer 3, the distinct layer is referred to as a hole transporting layer 6, and furthermore, when there is a distinct layer between the light emitting layer 1 and the electron injecting layer 5, the distinct layer is referred to as an electron transporting layer 7. It is to be noted that reference numeral 8 denotes a substrate in FIG. 1.

For the low molecular weight-type organic EL elements, films are formed by a vapor deposition method, and multi-layered elements can be thus easily achieved by carrying out vapor deposition while sequentially changing compounds used. On the other hand, for the high molecular weight-type organic EL elements, films are formed with the use of a wet process such as printing or ink-jet printing, and a problem is thus caused which is that the lower layer is dissolved when the upper layer is applied. Therefore, it is difficult to achieve multi-layered high molecular weight-type organic EL elements, as compared with the low molecular weight-type organic EL elements, and it has not been possible to achieve the effect of improving the luminescent efficiency or improving the lifetime.

In order to address this problem, several methods have been ever proposed. One of the methods is a method of using a difference in solubility. For example, there is an element that has a two-layer structure of: a hole-injecting layer of water-soluble polythiophene:poly(styrene sulfonate) (PEDOT:PSS); and a light emitting layer formed with the use of an aromatic organic solvent such as toluene. In this case, the PEDOT:PSS layer is not dissolved in the aromatic solvent such as toluene, and it is thus possible to prepare the two-layer structure.

Patent Literature 2 discloses, in order to overcome such a problem, a method of insolubilizing thin films against solvents by changing the solubility of a compound through the use of polymerization reactions of siloxane compounds, oxetane groups, vinyl groups, etc.

Although these methods for multi-layers are important, there are problems such as the need to remove water remaining in thin films in the case of using the water-soluble PEDOT:PSS, available materials limited for the use of the difference in solubility, and instability of siloxane compounds with moisture in air, and the problem of inadequate element characteristics.

While it is desirable to increase the number of organic layers and separate the functions of the respective layers in order to improve organic EL elements in efficiency and lifetime, there is a need to keep the lower layer from being dissolved in the formation of the upper layer as described above in order to increase the number of organic layers with the use of a wet process which easily forms films even for large area, and approaches have been adopted in which the solubility in a solvent is changed through the use of a polymerization reaction.

Furthermore, for lowering the driving voltages of organic EL elements, attempts have been made to improve the charge transporting performance of a charge transporting compound through the addition of an electron accepting compound to the charge transporting compound, but the performance has not been adequate yet.

On the other hand, the ink compositions which use the materials have problems such as the need for treatment at high temperature for curing and thus difficulty in applying resin substrates, or the need for heating for a long period of time and thus low productivity.

CITATION LIST

Patent Literature

Patent Literature 1: JP 2006-233162 A
Patent Literature 2: WO 2008/010487 A

SUMMARY OF INVENTION

Technical Problem

In view of the problems mentioned above, an object of the present invention is to provide an organic electronic material which is excellent in curability in the case as an ink composition, and able to prepare an organic electronic element capable of reducing the driving voltage and of being driven stably for a long period of time, and an ink composition including the organic electronic material.

Furthermore, another object of the present invention is to provide an organic electronic element and an organic EL element which include a layer with charge transporting performance better than ever before.

Solution to Problem

The inventors have, as a result of earnest studies, found that a material according to the present invention, which is obtained by combining an ionic compound that has a specific structure with a compound including a charge transporting unit, can solve some of the problems mentioned above, thereby completing the present invention.

More specifically, the present invention is characterized by the following aspects <1> to <11>.
<1> An organic electronic material comprising at least an ionic compound represented by the following general formula (1), and a compound including a charge transporting unit (hereinafter, referred to as a charge transporting compound).

[Chemical Formula 1]

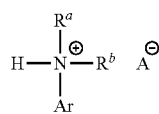

General Formula (1)

[In the general formula (1), Ar represents an aryl group or a heteroaryl group, $R^a$ to $R^b$ each independently represent a hydrogen atom (H), an alkyl group, a benzyl group, an aryl group, or a heteroaryl group, and Ar, $R^a$ and $R^b$ may be linked to each other to form a ring. However, at least one of $R^a$ to $R^b$ is any of a hydrogen atom (H), an alkyl group, and a benzyl group. A represents an anion.]
<2> The organic electronic material according to <1>, wherein the anion is represented by the following formulas (1b) to (5b).

[Chemical Formula 2]

 (1b)

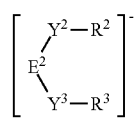 (2b)

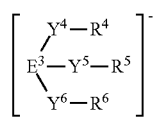 (3b)

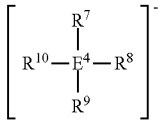 (4b)

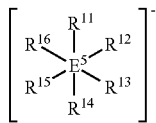 (5b)

[In the general formulas (1b) to (5b), $Y^1$ to $Y^6$ each independently represent a divalent linking group, and $R^1$ to $R^{16}$ each independently represent an electron attractive organic substituent (these structures may further have substituents and hetero atoms therein, and $R^2$ and $R^3$, $R^4$ to $R^6$, $R^7$ to $R^{10}$, or $R^{11}$ to $R^{16}$ may be each linked to form a ring or a polymer). $E^1$, $E^2$, $E^3$, $E^4$, and $E^5$ respectively represent an oxygen atom, a nitrogen atom, a carbon atom, a boron atom or a gallium atom, and a phosphorus atom or an antimony atom.]
<3> The organic electronic material according to <1> or <2>, wherein the charge transporting unit is an aromatic amine, a carbazole, or a thiophene.
<4> The organic electronic materials according to <1> to <3>, wherein the charge transporting compound is a polymer or an oligomer.
<5> The organic electronic material according to any of <1> to <4>, wherein the charge transporting compound includes one or more polymerizable substituents.
<6> The organic electronic material according to <5>, wherein the polymerizable substituents are any of an oxetane group, an epoxy group, and a vinyl ether group.
<7> An ink composition comprising the organic electronic material according to any of <1> to <6> and a solvent.
<8> An organic electronic element including a layer formed by an application method with the use of the organic electronic material according to any one of <1> to <6> or the ink composition according to claim 7.
<9> The organic electronic element according to <8>, wherein the layer formed by the application method is polymerized for insolubilization.
<10> The organic electronic element according to <9>, wherein another layer is further formed on the insolubilized layer to provide a multi-layer.
<11> The organic electronic element according to any of <8> to <10>, wherein the substrate is a resin film.

Advantageous Effects of Invention

The present invention can provide an organic electronic material which is excellent in curability in the case as an ink composition, and able to prepare, at a high yield, an organic electronic element capable of reducing the driving voltage and of being driven stably for a long period of time, and an ink composition including the organic electronic material.

Further, the present invention can provide an organic electronic element and an organic EL element which include a layer with charge transporting performance better than ever before.

BRIEF DESCRIPTION OF DRAWINGS

FIG. 1 is a schematic diagram illustrating an example of a multi-layered organic EL element.

DESCRIPTION OF EMBODIMENTS

<Organic Electronic Material>

An organic electronic material according to the present invention is characterized in that it contains at least an ionic compound represented by the following general formula (1), and a compound including a charge transporting unit (hereinafter, referred to as a charge transporting compound).

[Chemical Formula 3]

General Formula (1)

[In the general formula (1), Ar represents an aryl group or a heteroaryl group, $R^a$ to $R^b$ each independently represent a hydrogen atom (H), an alkyl group, a benzyl group, an aryl group, or a heteroaryl group, and Ar, $R^a$ and $R^b$ may be linked to each other to form a ring. However, at least one of $R^a$ to $R^b$ is any of a hydrogen atom (H), an alkyl group, and a benzyl group. A represents an anion.]

In the present invention, the ionic compound represented by the general formula (1) is characterized in that at least one of the four substituents N is a hydrogen atom, and at least one thereof is an aryl group. The use of the ionic compound improves curability at low temperatures when the compound is used as a polymerization initiator. In addition, a stacked element obtained through the use of an application method can be prepared by the combination with a compound including a polymerizable substituent. Moreover, a film formed from an ink composition including the ionic compound is high in charge transporting capacity, and useful in organic electronic applications.

In this case, in order to increase the solubility as an ink composition in a solvent, at least one of $R^a$ to $R^b$ is preferably an alkyl group, a benzyl group, an aryl group, or a heteroaryl group (where either one of $R^a$ to $R^b$ is an alkyl group or a benzyl group), and more preferably, both of $R^a$ to $R^b$ are an alkyl group or a benzyl group. It is to be noted that there is no case where both of $R^a$ to $R^b$ are an aryl group or a heteroaryl group.

The alkyl group may be straight, branched, or cyclic, may have substituents, and typically has approximately 1 to 20 carbon atoms, and specific examples of the alkyl group include a methyl group, an ethyl group, a propyl group, an i-propyl group, a butyl group, an i-butyl group, a t-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoroethyl group, a perfluorobutyl group, a perfluorohexyl group, and a perfluorooctyl group.

The aryl group is an atom group of an aromatic hydrocarbon with one hydrogen atom removed therefrom. Examples of the aromatic hydrocarbon herein include hydrocarbons with a condensed ring, and two or more independent benzene rings or condensed rings linked directly or through a group such as vinylene. In addition, the aryl group may have substituents, and typically has approximately 6 to 60 carbon atoms, specifically, examples of the aryl group include a phenyl group, C1 to C12 alkoxyphenyl groups (C1 to C12 refer to 1 to 12 carbon atoms of substituents; the same shall apply hereafter), C1 to C12 alkylphenyl groups, a 1-naphthyl group, a 2-naphthyl group, a 1-anthracenyl group, a 2-anthracenyl group, a 9-anthracenyl group, a phenanthrene-yl group, a pyrene-yl group, a perylene-yl group, and a pentafluorophenyl group, and the C1 to C12 alkoxyphenyl groups and C1 to C12 alkylphenyl groups are preferred. Examples of the C1 to C12 alkoxy specifically include methoxy, ethoxy, propyloxy, i-propyloxy, butoxy, butoxy, t-butoxy, pentyloxy, hexyloxy, cyclohexyloxy, heptyloxy, octyloxy, 2-ethylhexyloxy, nonyloxy, decyloxy, 3,7-dimethyloctyloxy, and lauryloxy. Examples of the C1 to C12 alkyl specifically include methyl, ethyl, propyl, i-propyl, butyl, i-butyl, t-butyl, pentyl, hexyl, cyclohexyl, heptyl, octyl, 2-ethylhexyl, nonyl, decyl, 3,7-dimethyloctyl, and lauryl.

The heteroaryl group refers to a remaining atom group of a heterocyclic compound with one hydrogen atom removed therefrom, and the group may have substituents. The non-substituted monovalent heterocyclic group typically has approximately 4 to 60, preferably 4 to 20 carbon atoms. Examples of the monovalent heterocyclic group include a thienyl group, C1 to C12 alkyl thienyl groups, a pyrrolyl group, a furyl group, a pyridyl group, and C1 to C12 alkylpyridyl groups, and the thienyl group and pyridyl group are preferred. The C1 to C12 alkyl thienyl groups, pyridyl group, and C1 to C12 alkylpyridyl groups are preferred.

While A is not particularly limited as long as it is a conventionally known anion, anions represented by the following general formulas (1b) to (5b) are preferred in manufacturing organic electronic elements, in particular, organic EL elements which are able to be reduced in driving voltage and stably driven for a long period of time.

[Chemical Formula 4]

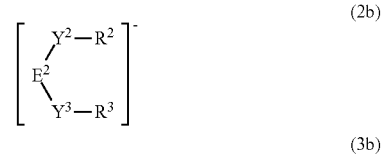

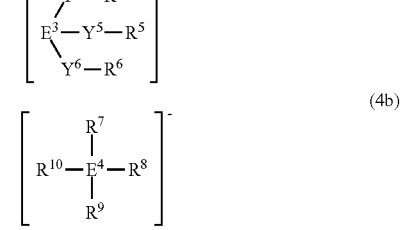

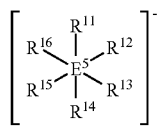
(5b)

[In the general formulas (1b) to (5b), $Y^1$ to $Y^6$ each independently represent a divalent linking group, and $R^1$ to $R^{16}$ each independently represent an electron attractive organic substituent (these structures may further have substituents and hetero atoms therein, and $R^2$ and $R^3$, $R^4$ to $R^6$, $R^7$ to $R^{10}$, or $R^{11}$ to $R^{16}$ may be each linked to form a ring or a polymer). $E^1$, $E^2$, $E^3$, $E^4$, and $E^5$ respectively represent an oxygen atom, a nitrogen atom, a carbon atom, a boron atom or a gallium atom, and a phosphorus atom or an antimony atom.]

Examples of the electron attractive organic substituents ($R^1$ to $R^{16}$ in the formulas) include: halogen atoms such as a fluorine atom, a chlorine atom, and a bromine atom; alkylsulfonyl groups such as a cyano group, a thiocyano group, a nitro group, and a mesyl group; arylsulfonyl groups such as a tosyl group; acyl groups typically having 1 to 12, preferably to 6 carbon atoms, such as a formyl group, an acetyl group, and a benzoyl group; alkoxycarbonyl groups typically having 2 to 10, preferably to 7 carbon atoms, such as a methoxycarbonyl group and an ethoxycarbonyl group; aryloxycarbonyl groups including an aromatic hydrocarbon group or an aromatic heterocyclic group typically having 3, preferably 4, to 25, preferably to 15 carbon atoms, such as a phenoxycarbonyl group and a pyridyloxycarbonyl group; acyloxy groups typically having 2 to 20 carbon atoms, such as an acetoxy group; haloalkyl, haloalkenyl, and haloalkynyl groups obtained by substituting, with a halogen atom such as a fluorine atom and a chlorine atom, straight, branched, or cyclic alkyl, alkenyl, and alkynyl groups typically having 1 to 10, preferably to 6 carbon atoms, such as an alkyloxysulfonyl group, an aryloxysulfonyl group, a trifluoromethyl group, and a pentafluoroethyl group; and haloaryl groups typically having 6 to 20 carbon atoms, such as a pentafluorophenyl group. Among these groups, from the perspective of being able to efficiently delocalize negative charges, more preferred are groups obtained by substituting, with halogen atoms such as fluorine, some or all of hydrogen atoms of the groups having hydrogen atoms among the organic groups mentioned above, for example, but not limited to, straight, branched, or cyclic perfluoroalkyl groups, perfluoroalkylsulfonyl groups, perfluoroaryl groups, perfluoroalkyloxysulfonyl groups, perfluoroarylsulfonyl groups, perfluoroaryloxysulfonyl groups, perfluoroacyl groups, perfluoroalkoxycarbonyl groups, perfluoroacyloxy groups, perfluoroaryloxycarbonyl groups, perfluoroalkenyl groups, and perfluoroalkynyl groups having 1 to 20 carbon atoms, which may include hetero atoms, as represented by the following group of structural formulas (1). Further, among these groups, preferred are straight and branched perfluoroalkyl groups having 1 to 8 carbon atoms, cyclic perfluoroalkyl groups having 3 to 6 carbon atoms, and perfluoroaryl groups having 6 to 18 carbon atoms.

Group of Structural Formulas (1)

[Chemical Formula 5]

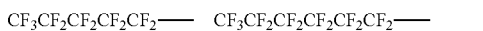

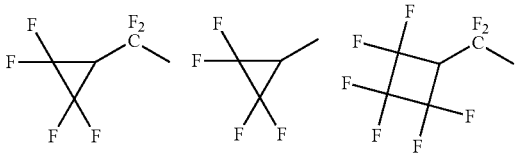

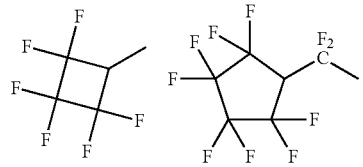

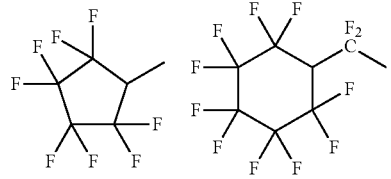

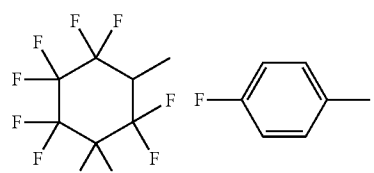

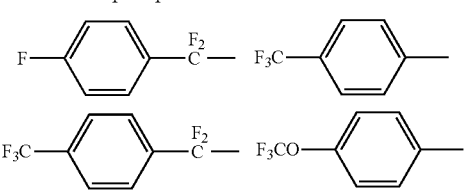

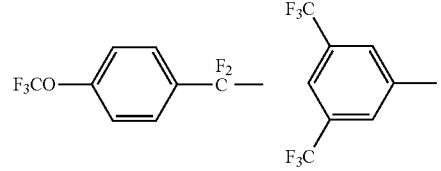

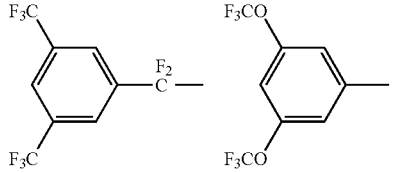

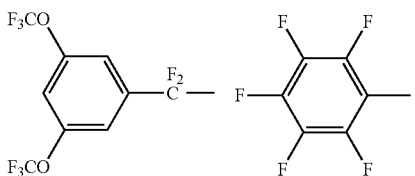

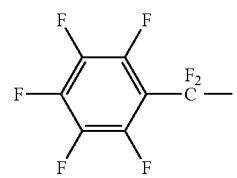

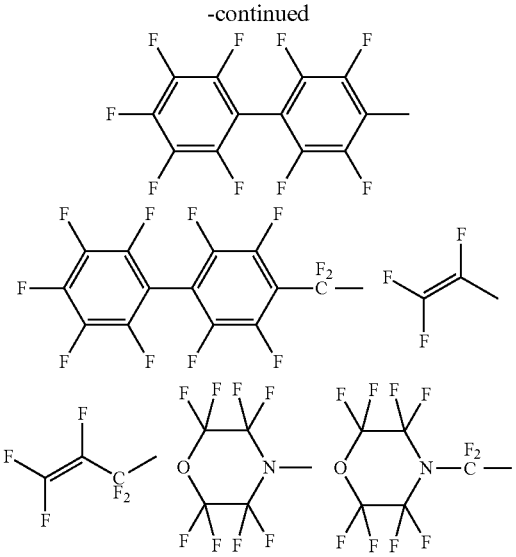

In addition, $Y^1$ to $Y^6$ in the general formulas represent a divalent linking group, specifically, which is preferably any one of the following formulas (1c) to (11c).

[Chemical Formula 6]

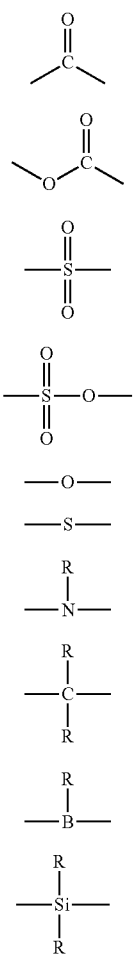

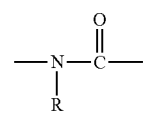

(In the formulas, R represents any organic group (these structures may further have substituents and hetero atoms therein).)

R in the general formulas (7c) to (11c) preferably represents, independently of each other, an alkyl group, an alkenyl group, an alkynyl group, an aromatic hydrocarbon group, or an aromatic heterocyclic group which may be substituted, from the perspective of improvement in electron acceptability and solubility in solvents, and more preferably an organic group having an electron attractive substituent among the previously mentioned substituents, and examples of the organic group include groups in the group of structural formulas (1).

In addition, the anion in the present invention preferably has a negative charge, but not particularly limited to, mainly on an oxygen atom, a nitrogen atom, a carbon atom, a boron atom, or a gallium atom, more preferably on an oxygen atom, a nitrogen atom, a carbon atom, or a boron atom, and most preferably represented by the following formula (12c), (13c), (14c), or (15c).

[Chemical Formula 7]

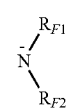

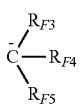

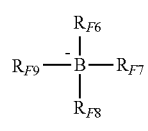

(In the formulas, $R_{F1}$ to $R_{F10}$ each independently represent an electron attractive organic substituent (these structures may further have substituents and hetero atoms therein, and $R_{F1}$ to $R_{F9}$ may be each linked to form a ring or a polymer), and examples of the organic substituent include, but not limited to, the groups represented by the group of structural formulas (1), for example.)

[Charge Transporting Compound]

The "charge transporting compound" in the present invention will be described in detail. In the present invention, the charge transporting compound refers to a compound including a charge transporting unit. In the present invention, the "charge transporting unit" refers to an atom group that has the ability to transport holes or electrons, and will be described below in detail.

The charge transporting unit only has to have the ability to transport holes or electrons, and is preferably, but not particularly limited to, an amine, a carbazole, or a thiophene having an aromatic ring. Specific examples thereof include those described in WO 2011/132702 A. Among these examples, in particular, the following amine structures (1) to (14) are preferred. While the meanings of E, Ar, and X in the following amine structures (1) to (14) are described in detail in the publication mentioned above, here are brief descriptions thereof.

E each independently represents —$R^1$, —$OR^2$, —$SR^3$, —$OCOR^4$, —$COOR^5$, or —$SiR^6R^7R^8$ (provided that $R^1$ to $R^8$ represent a hydrogen atom, a straight, cyclic, or branched alkyl group having 1 to 22 carbon atoms, or an aryl group or a heteroaryl group having 2 to 30 carbon atoms), and Ar each independently represents an arylene group or a heteroarylene group having 2 to 30 carbon atoms. The arylene group and heteroaryl group may have substituents. X and Z each independently a divalent linking group, which is preferably, but not limited to, a group obtained by further removing one hydrogen atom from the group having one or more hydrogen atoms among the previously mentioned groups R. x represents an integer of 0 to 2. Y represents a trivalent linking group, which represents a group obtained by removing two hydrogen atoms from the group having two or more hydrogen atoms among the previously mentioned R.

[Chemical Formula 8]

$$E-Ar-\underset{\underset{E}{\overset{|}{Ar}}}{N}-Ar-E \quad (1)$$

$$E-Ar-\underset{\underset{E}{\overset{|}{Ar}}}{N}-Ar-\underset{\underset{E}{\overset{|}{Ar}}}{N}-Ar-E \quad (2)$$

$$E-Ar-\underset{\underset{E}{\overset{|}{Ar}}}{N}-Ar-Ar-E \quad (3)$$

$$E-Ar-\underset{\underset{E}{\overset{|}{Ar}}}{N}-Ar-Ar-\underset{\underset{E}{\overset{|}{Ar}}}{N}-Ar-E \quad (4)$$

$$E-Ar-\underset{\underset{E}{\overset{|}{Ar}}}{N}-Ar-\underset{\underset{E}{\overset{|}{Ar}}}{N}-Ar-Ar-E \quad (5)$$

$$E-Ar-\underset{\underset{E}{\overset{|}{Ar}}}{N}-Ar-Ar-\underset{\underset{E}{\overset{|}{Ar}}}{N}-Ar-Ar-E \quad (6)$$

$$E-Ar-\underset{\underset{E}{\overset{|}{Ar}}}{N}-Ar-X-Ar-\underset{\underset{E}{\overset{|}{Ar}}}{N}-Ar-E \quad (7)$$

$$E-Ar-\underset{\underset{E}{\overset{|}{Ar}}}{N}-Ar-X-Ar-\underset{\underset{E}{\overset{|}{Ar}}}{N}-Ar-Ar-E \quad (8)$$

$$\begin{array}{c}E-Ar-\underset{|}{N}-Ar-E\\|\\Ar\\|\\E-Ar-\underset{|}{N}-Ar-E\end{array} \quad (9)$$

$$\begin{array}{c}E-Ar-\underset{|}{N}-Ar-E\\|\\Ar\\|\\Ar\\|\\E-Ar-\underset{|}{N}-Ar-E\end{array} \quad (10)$$

$$\begin{array}{c}E-Ar-\underset{|}{N}-Ar-Ar-E\\|\\Ar\\|\\E-Ar-\underset{|}{N}-Ar-E\end{array} \quad (11)$$

$$\begin{array}{c}E-Ar-\underset{|}{N}-Ar-E\\|\\Ar\\|\\X\\|\\Ar\\|\\E-Ar-\underset{|}{N}-Ar-E\end{array} \quad (12)$$

$$\begin{array}{c}E-Ar-\underset{|}{N}-Ar-Ar-E\\|\\Ar\\|\\Ar\\|\\E-Ar-\underset{|}{N}-Ar-E\end{array} \quad (13)$$

$$\begin{array}{c}E-Ar-\underset{|}{N}-Ar-Ar-E\\|\\Ar\\|\\X\\|\\Ar\\|\\E-Ar-\underset{|}{N}-Ar-E\end{array} \quad (14)$$

In addition, the charge transporting compound in the present invention is not particularly limited, which may be commercially available compounds, or synthesized by methods known to one skilled in the art.

In addition, the charge transporting compound in the present invention may be a low molecular weight compound, or may be a high molecular weight compound such as a polymer or an oligomer. The high molecular weight compound such as a polymer or an oligomer is preferred from the perspective of solubility in organic solvents, whereas the low molecular weight compound is preferred from the perspective of easy purification by sublimation or recrystallization.

When the charge transporting compound in the present invention is a polymer or an oligomer, a polymer or an oligomer that has a structure branched in three or more directions is preferred from the perspective of lowering the temperature for progressing an adequate polymerization reaction. In addition, this branched structure can increase the glass transition temperature of the polymer or oligomer, and thus also makes a contribution to an improvement in the heat resistance of the polymer or oligomer.

This branched structure means that when a chain with the highest degree of polymerization is regarded as a main chain among various chains in a molecule of the polymer or oligomer, a side chain with the same degree of polymerization or a lower degree of polymerization is linked to the main chain. The degree of polymerization in the present invention refers to the number of monomer units for use in synthesizing the polymer or oligomer, which are contained per molecule of the polymer or oligomer. The side chain in the present invention refers to a chain including at least one or more polymerization units, which is different from the main chain of the polymer or oligomer, and the other chains are regarded as not side chains but substituents.

The method for forming the branched structure is not particularly limited, but the polymer or oligomer may be formed with the use of a monomer that has three or more polymerizable sites in a molecule, or formed by forming linear polymers or oligomers, followed by the polymerization of the polymers or oligomers with each other.

Specifically, any one of structures of the following general formulas (1) to (10) is preferably included as an origin unit for forming the branched structure in the polymer or oligomer.

[Chemical Formula 9]

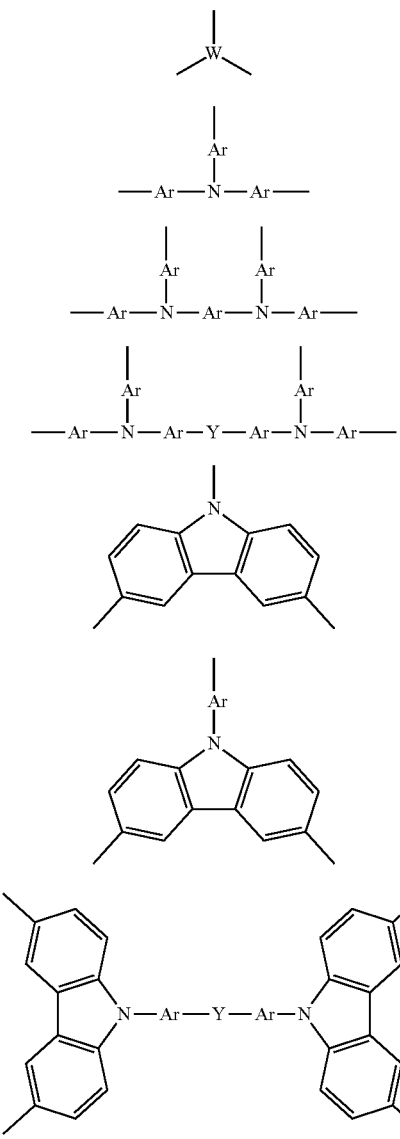

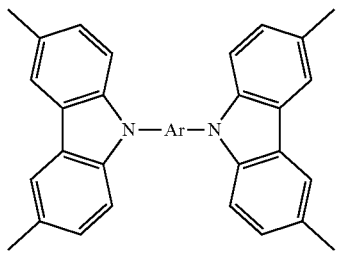

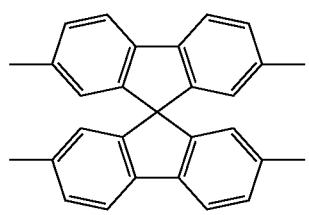

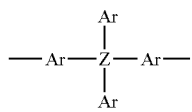

(In the formulas, Ar each independently represents a divalent linking group, and represents an arylene group or a heteroarylene group having 2 to 30 carbon atoms. The arylene group is an atom group of an aromatic hydrocarbon with two hydrogen atoms removed therefrom, which may have substituents, and examples thereof include, for example, phenylene, biphenyl-diyl, terphenyl-diyl, naphthalene-diyl, anthracene-diyl, tetracene-diyl, fluorene-diyl, and phenanthrene-diyl. The heteroarylene group is an atom group of an aromatic compound having a hetero atom with two hydrogen atoms removed therefrom, which may have substituents, and examples thereof include, for example, pyridine-diyl, pyrazine-diyl, quinoline-diyl, isoquinoline-diyl, acridine-diyl, phenanthroline-diyl, furan-diyl, pyrrole-diyl, thiophene-diyl, oxazole-diyl, oxadiazole-diyl, thiadiazole-diyl, triazole-diyl, benzoxazole-diyl, benzoxadiazole-diyl, benzothiadiazole-diyl, benzotriazole-diyl, and benzothiophene-diyl. W represents a trivalent linking group, which is an atom group of the arylene group or heteroarylene group with one hydrogen atom further removed therefrom, which may have substituents. Y each independently represents a divalent linking group. Z represents any of a carbon atom, a silicon atom, and a phosphorus atom.)

Y in the general formulas (4) and (7) is preferably a divalent linking group represented by the following formulas.

[Chemical Formula 10]

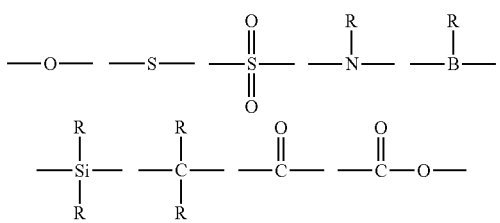

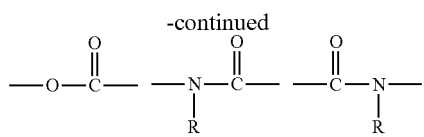

(In the formula, R each independently represents a hydrogen atom, a straight, cyclic, or branched alkyl group having 1 to 22 carbon atoms, or an aryl group or a heteroaryl group having 2 to 30 carbon atoms. In this case, the aryl group is an atom group of an aromatic hydrocarbon with one hydrogen atom removed therefrom, which may have substituents, whereas the heteroaryl group is an atom group of an aromatic compound having a hetero atom with one hydrogen atom removed therefrom, which may have substituents.)

Furthermore, the charge transporting compound in the present invention preferably has one or more "polymerizable substituents", in order to change the solubility to prepare a stacked structure of organic thin films. The "polymerizable substituents" herein refers to substituents which are able to form bonds between two or more molecules by developing a polymerization reaction, and will be described below in detail.

Examples of the polymerizable substituents include groups having a carbon-carbon multiple bond (examples thereof can include, for example, a vinyl group, an acetylene group, a butenyl group, an acrylic group, an acrylate group, an acrylamide group, a methacrylic group, a methacrylate group, a methacrylamide group, an arene group, an allyl group, a vinyl ether group, a vinyl amino group, a furyl group, a pyrrole group, a thiophene group, and a silole group), groups having a small ring (for example, a cyclopropyl group, a cyclobutyl group, an epoxy group, an oxetane group, a diketene group, an episulfide group), and groups containing a lactone group, a lactam group, or a siloxane derivative. Further, in addition to the groups mentioned above, groups which are able to form an ester linkage or an amide linkage can be also used in combination. The combinations include, for example, combinations such as an ester group and an amino group, and an ester group and a hydroxyl group. As the polymerizable substituents, in particular, an oxetane group, an epoxy group, a vinyl group, a vinylether group, an acrylate group, and a methacrylate group are preferred from the perspective of reactivity, and an oxetane group is most preferred. From the perspective of increasing the degree of freedom of the polymerizable substituents to make a curing reaction likely to be developed, the main chain of the polymer or oligomer and the polymerizable substituents are more preferably linked through an alkyl chain having 1 to 8 carbon atoms.

In addition, the polymer or oligomer in the present invention may be copolymers having, as copolymerization repeating units, structures represented by the following group of structural formulas (X) as the arylene group or heteroarylene group, in addition to repeating units represented by the general formulas (1a) to (84a) described in WO 2011/132702 A mentioned previously, in order to adjust the solubility, heat resistance, or electrical properties. In this case, the copolymer may be a random, block, or graft copolymer, or may be a polymer which has an intermediate structure between the copolymers, for example, a block-like random copolymer. In addition, the polymer or oligomer for use in the present invention may be branched in the main chain, with three or more terminals. It is to be noted that R in the group of structural formulas (X) each independently represents a hydrogen atom, a straight, cyclic, or branched alkyl group having 1 to 22 carbon atoms, or an aryl group or a heteroaryl group having 2 to 30 carbon atoms.

[Group of Structural Formulas (X)]

[Chemical Formula 11]

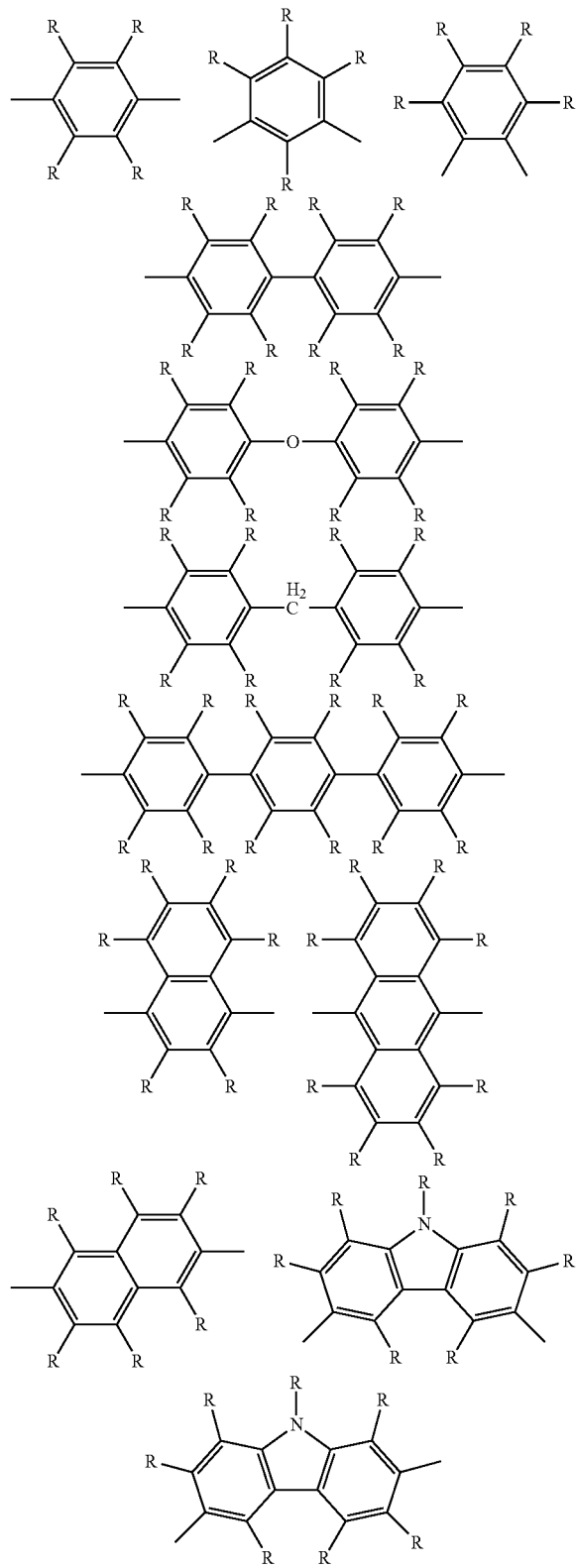

-continued

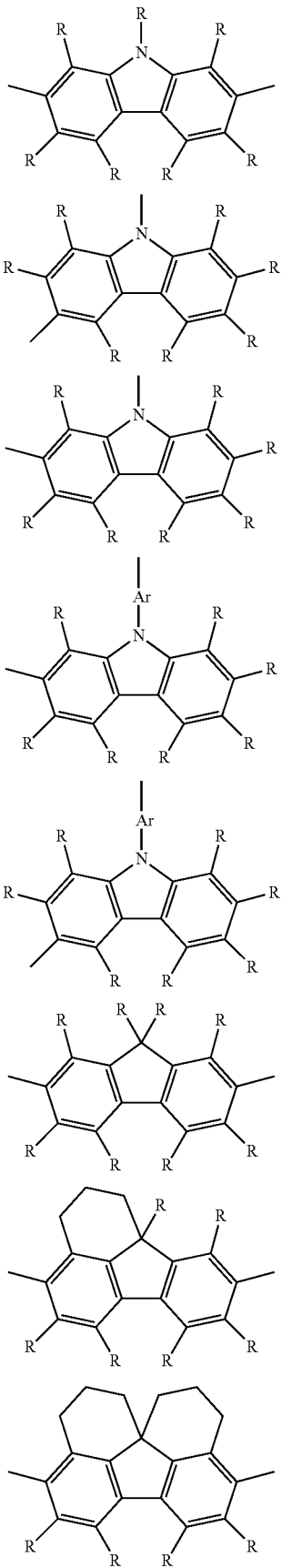

-continued

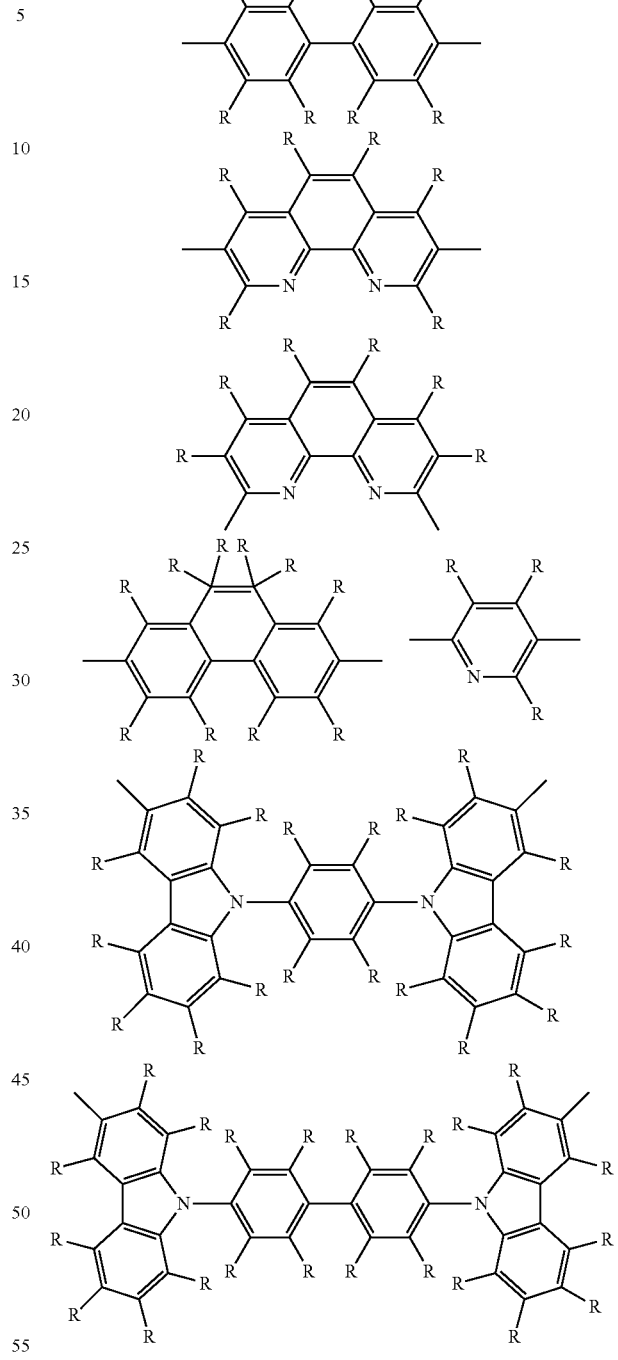

In addition, when the charge transporting compound is a polymer or an oligomer, the number average molecular weight is preferably 1,000 or more and 1,000,000 or less from the perspective of solubility in solvents and film formation property. The number average molecular weight is more preferably 2,000 or more and 900,000 or less, further preferably 3,000 or more and 800,000 or less. The number average molecular weight less than 1,000 makes the compound likely to be crystallized, thereby resulting in deterioration of film formation property. In addition, the molecular weight more than 1,000,000 decreases the solubility in solvents, thereby making it difficult to prepare an applied solution or an applied ink.

In addition, the organic electronic material according to the present invention preferably includes a polymerization initiator, in order to utilize the difference in solubility caused by a polymerization reaction.

The polymerization initiator is not particularly limited as long as the initiator shows the ability to polymerize the polymerizable substituents by applying heat, light, microwaves, radiation, electron beams, or the like but preferably a polymerization initiator which initiates polymerization by light irradiation and/or heating.

In addition, the ionic compound according to the present invention can be used alone as a polymerization initiator.

In order to form various types of layers for use in organic electronic elements and the like with the use of the organic electronic material according to the present invention, for example, a solution (ink composition) containing the organic electronic material according to the present invention can be applied onto a desired base body by a known method such as, for example, an ink-jet method, a casting method, a dipping method, printing methods, e.g., relief printing, intaglio printing, offset printing, planographic printing, relief reverse offset printing, screen printing, and gravure printing, a spin coating method, and then subjected to light irradiation, heat treatment, or the like to progress a polymerization reaction of the polymer or oligomer, and change the solubility of the applied layer (curing). The repetition of such work makes it possible to increase the number of layers for high-molecular type organic electronic elements and organic EL elements.

The application method as described above can be typically implemented in the temperature range of −20 to +300° C., preferably 10 to 100° C., particularly preferably 15 to 50° C., and examples of the solvent for use in the solution described above include, but not particularly limited to, for example, solvents for use in the preparation of an ink composition as will be described later.

In addition, for the light irradiation mentioned above, light sources can be used such as low-pressure mercury vapor lamps, medium-pressure mercury vapor lamps, high-pressure mercury vapor lamps, ultrahigh-pressure mercury vapor lamps, metal halide lamps, xenon lamps, fluorescent lights, light emitting diodes, and sunlight.

In addition, the heat treatment can be carried out on a hot plate or in an oven, and in particular, in the present invention, the use of the ionic compound described above allows for (1) curing at low temperatures and (2) curing for a short period of time, because of excellence in curability. The curing at low temperatures makes a contribution to the use of resin substrates and the like which have low heatproof temperatures, whereas the curing for a period of time makes a contribution to an improvement in productivity.

Specifically, when the heating time is supposed to be 60 minutes in the case of (1) mentioned above, curing can be carried out at the heating temperature in the temperature range of 0 to 300° C., preferably 50 to 250° C., particularly preferably 50 to 200° C. When the heating temperature is supposed to be 180° C. in the case of (2) mentioned above, the heating time is preferably 1 to 60 minutes, and preferably 1 to 20 minutes.

<Ink Composition>

An ink composition according to the present invention is characterized in that it contains the already described organic electronic material according to the present invention, and a solvent, and may contain other additives, for example, a polymerization inhibitor, a stabilizer, a thickener, a gelator, a flame retardant, an antioxidant, an antireductant, an oxidant, a reductant, a surface modifier, an emulsifier, an antifoamer, a dispersant, and a surfactant. Examples of the solvent include: water; alcohols such as methanol, ethanol, and isopropyl alcohol; alkanes such as pentane, hexane, and octane; cyclic alkanes such as cyclohexane; aromatic solvents such as benzene, toluene, xylene, mesitylene, tetralin, and diphenylmethane; aliphatic ethers such as ethylene glycol dimethyl ether, ethylene glycol diethyl ether, and propylene glycol-1-monomethyl ether acetate; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole; aliphatic esters such as ethyl acetate, n-butyl acetate, ethyl lactate, and n-butyl lactate; aromatic esters such as phenyl acetate, phenyl propionate, methyl benzoate, ethyl benzoate, propyl benzoate, and n-butyl benzoate; amide solvents such as N,N-dimethylformamide and N,N-dimethylacetoamide; and other solvents such as dimethyl sulfoxide, tetrahydrofuran, acetone, chloroform, and methylene chloride, and preferably, aromatic solvents, aliphatic esters, aromatic esters, aliphatic ethers, and aromatic ethers can be used.

In the ink composition according to the present invention, the content of the organic electronic material with respect to the solvent is preferably 0.1 to 30 mass % from the perspective of being applicable to various application processes.

<Organic Electronic Element, Organic Electroluminescent Element>

An organic electronic element according to the present invention includes a layer formed by an application method with the use of the organic electronic material or ink composition mentioned above, and further an insolubilized layer obtained by polymerizing the formed layer.

Likewise, an organic electroluminescent element (organic EL element) according to the present invention includes a layer formed with the use of the organic electronic material or ink composition mentioned above, and further an insolubilized layer obtained by polymerizing the formed layer.

The elements each include the excellent layer formed with the use of the organic electronic material according to the present invention, and has a lower driving voltage and a longer emission lifetime than ever before.

An EL element according to the present invention will be described below in detail.

[Organic EL Element]

The organic EL element according to the present invention is not particularly limited as long as the element includes a light emitting layer, a polymerized layer, an anode, a cathode, and a substrate, but may have other layers such as a hole injecting layer, an electron injecting layer, a hole transporting layer, and an electron transporting layer. Further, the hole injecting layer, hole transporting layer, or light emitting layer is preferably a layer formed with the use of the organic electronic material or ink composition according to the present invention.

The respective layers will be described below in detail.

(Light Emitting Layer)

The material for use in the light emitting layer may be a low molecular weight compound or may be a polymer or an oligomer, and it is also possible to use dendrimers and the like. Low molecular weight compounds which use fluorescence emissions include perylene, coumarin, rubrene, quinacridone, dyes for dye laser (for example, rhodamine, DCM1, etc.), aluminum complexes (for example, Tris(8- hydroxyquinolinato)aluminum (III) (Alq$_3$)), stilbene, and derivatives thereof. Polyfluorene, polyphenylene, polyphenylenevinylene (PPV), polyvinylcarbazole (PVK), a fluorene-benzothiadiazole copolymer, a fluorene-triphenylamine copolymer, and derivatives and mixtures thereof can be used in a preferred manner as polymers or oligomers which use fluorescence emissions.

On the other hand, in recent years, phosphorescent organic EL elements have been also actively developed in order to achieve higher-efficiency organic EL elements. Phosphorescent organic EL elements are able to use not only energy in singlet states, but also energy in triplet states, and increase the internal quantum yields up to 100% in principle. In the case of phosphorescent organic EL elements, a host material is doped with a phosphorescent material of metal complex including a heavy metal such as platinum or iridium as a dopant that produces phosphorescence to extract phosphorescent emissions (see M. A. Baldo et al., Nature, vol. 395, p. 151 (1998), M. A. Baldo et al., Applied Physics Letters, vol. 75, p. 4 (1999), M. A. Baldo et al., Nature, vol. 403, p. 750 (2000)).

Also in the case of the organic EL element according to the present invention, it is preferable to use a phosphorescent material for the light emitting layer, from the perspective of higher efficiency. As the phosphorescent material, metal complexes and the like including a central metal such as Ir or Pt can be used in a preferred manner. Specifically, Ir complexes include, for example, FIr(pic)[iridium (III) bis [(4,6-difluorophenyl)-pyridinato-N,C$^2$]picolinate] which emits blue light, Ir(ppy)$_3$[fac tris(2-phenylpyridine)iridium] (see M. A. Baldo et al., Nature, vol. 403, p. 750 (2000) mentioned previously) which emits green light, or (btp)$_2$Ir (acac){bis[2-(2'-benzo[4,5-α]thienyl)pyridinato-N,C3] iridium(acetyl-acetonate)} and Ir(piq)$_3$[tris(1-phenylisoquinoline)iridium] which emit red light, as mentioned in Adachi et al., Appl. Phys. Lett., 78 No. 11, 2001, 1622.

Pt complexes include, for example, 2,3,7,8,12,13,17,18-octaethyl-21H,23H-porphyrinplatinum (PtOEP) which emits red light.

Low molecular or dendrite types, for example, iridium cored dendrimers can be used for the phosphorescent material. Furthermore, derivatives of these materials can be also used in a preferred manner.

In addition, when a phosphorescent material is included in the light emitting layer, the layer preferably includes a host material in addition to the phosphorescent material.

The host material may be a low molecular weight compound or a high molecular weight compound, and dendrimers and the like can be also used as the host material.

For example, CBP (4,4'-Bis(Carbazol-9-yl)-biphenyl), mCP (1,3-bis(9-carbazolyl)benzene), and CDBP (4,4'-Bis (Carbazol-9-yl)-2,2'-dimethylbiphenyl) can be used as the low molecular weight compound, whereas, for example, polyvinylcarbazole, polyphenylene, and polyfluorene can be used as the high molecular weight compound, and derivatives thereof can be also used.

The light emitting layer may be formed by a vapor deposition method, or may be formed by an application method.

In the case of the formation by an application method, the organic EL element can be inexpensively manufactured, which is more preferred. In order to form the light emitting layer by an application method, a solution containing the phosphorescent material, and if necessary, a host material can be applied onto a desired base body by a known method such as, for example, an ink-jet method, a casting method, a dipping method, printing methods, e.g., relief printing, intaglio printing, offset printing, planographic printing, relief reverse offset printing, screen printing, and gravure printing, a spin coating method.

(Cathode)

The cathode material is preferably, for example, a metal or a metal alloy such as Li, Ca, Mg, Al, In, Cs, Ba, Mg/Ag, LiF, or CsF.

(Anode)

Metals (for example, Au) or other materials with metallic conductivity, for example, oxides (for example, ITO:indium oxide/tin oxide) and conductive polymers (for example, a mixture of polythiophene-polystyrene sulfonate (PEDOT: PSS)), also can be used as the anode.

(Electron Transporting Layer, Electron Injecting Layer)

Examples of the electron transporting layer and electron injecting layer include, for example, phenanthroline derivatives (for example, 2,9-dimethyl-4,7-diphenyl-1,10-phenanthroline (BCP)), bipyridine derivatives, nitro-substituted fluorene derivatives, diphenylquinone derivatives, thiopyrandioxide derivatives, heterocyclic tetracarboxylic anhydrides such as naphthaleneperylene, carbodiimide, fluorenylidene methane derivatives, anthraquinonedimethane and anthrone derivatives, oxadiazole derivatives (2-(4-Biphenylyl)-5-(4-tert-butylphenyl-1,3,4-oxadiazole)(PBD)), and aluminum complexes (for example, Tris(8-hydroxyquinolinato)aluminum (III) (Alq$_3$)). Furthermore, in association with the oxadiazole derivatives mentioned above, thiadiazole derivatives with a sulfur atom substituted for an oxygen atom of an oxadiazole ring and quinoxaline derivatives having a quinoxaline ring known as an electron attractive group can be also used.

(Substrate)

The substrate which can be used for the organic EL element according to the present invention is not particularly limited on the type such as glass or plastic, or not particularly limited as long as the substrate is transparent, but glass, quartz, light transmissive resin films, etc. are used preferably. In the case of using a resin film (flexible substrate), it is possible to provide the organic EL element with flexibility, which is particularly preferred.

Examples of the resin film include films composed of, for example, polyethylene terephthalate (PET), polyethylene naphthalate (PEN), polyethersulfone (PES), polyetherimide, polyether ether ketone, polyphenylenesulfide, polyarylate, polyimide, polycarbonate (PC), cellulose triacetate (TAC), or cellulose acetate propionate (CAP).

In addition, in the case of using the resin film, in order to suppress permeation of water vapor, oxygen, etc., the resin film may be coated with an inorganic substance such as silicon oxide or silicon nitride and used.

(Luminescent Color)

While the luminescent color is not to be considered particularly limited in the organic EL element according to the present invention, white light emitting elements are preferred because the elements can be used for various types of lighting devices such as domestic lighting, in-car lighting, and backlights for watches and liquid crystals.

As a method for forming a white light emitting element, multiple luminescent materials are used to simultaneously produce and mix multiple luminescent colors for obtaining a white light emission, because it is currently difficult to produce a white light emission with a single material. While the combination of multiple luminescent colors is not to be considered particularly limited, examples thereof include a combination containing three emission maximum wavelengths for blue, green, and red, and a combination containing two emission maximum wavelengths, which uses a complementary relationship such as blue and yellow or as greenish yellow and orange. In addition, the luminescent color can be controlled by adjusting the type and amount of the luminescent materials.

<Display Element, Lighting Device, Display Device>

A display element according to the present invention is characterized in that it includes the already described organic EL element according to the present invention.

For example, a color display element is obtained by the use of the organic EL element according to the present invention as elements corresponding to respective pixels for red, green, and blue (RGB).

Types of image formation includes: a simple matrix type for directly driving individual organic EL elements arranged on a panel with electrodes arranged in a matrix form; and an active matrix type for driving thin film transistors arranged for each element. The former is used to display characters and the like, because the number of vertical pixels is limited although the structure is simple. The latter is used for high-definition display, because bright high-definition images are obtained with a small amount of current at a low driving voltage.

In addition, a lighting device according to the present invention is characterized in that it includes the already described organic EL element according to the present invention. Furthermore, a display device according to the present invention is characterized in that it includes the lighting device and a liquid crystal element as a display means. The display device may be a display device, that is, a liquid crystal display device which uses the lighting device according to the present invention as a backlight (white light emitting light source) and uses a liquid crystal element as a display means. This configuration refers to a known liquid crystal display device in which only a backlight is replaced with the lighting device according to the present invention, and known techniques can be diverted to the liquid crystal element section.

EXAMPLES

The present invention will be further specifically described below with reference to examples, but is not to be considered limited to the following examples.

[Synthesis of Ionic Compound 1]

The mixture of 1.7 g of hydrobromic acid (48%) with 2.1 g (0.01 mol) of N-Benzyl-N-ethylaniline (I) was slightly heated, shaken up, left for 1 hour, and then subjected to water removal under reduced pressure to provide a viscous oily matter. Checking by proton NMR confirmed the disappearance of N-Benzyl-N-ethylaniline (I) and the generation of N-Benzyl-N-ethylanilinium bomide (II). Then, 1.46 g (0.005 mol) of (II) mentioned above and 35.1 g (0.005 mol) of sodium tetrakis(pentaphenyl)borate (10% aq.) were mixed and stirred. The mixture was left overnight, and a bluish white precipitate was found in white turbid jelly as a whole. This precipitate was, with the appropriate addition of water thereto, subjected to filtration under reduced pressure, washed with water, and dried to obtain a blue-white solid (yield 1.7 g/reaction yield 39%).

Here is the reaction formula of the reaction mentioned above.

[Chemical Formula 12]

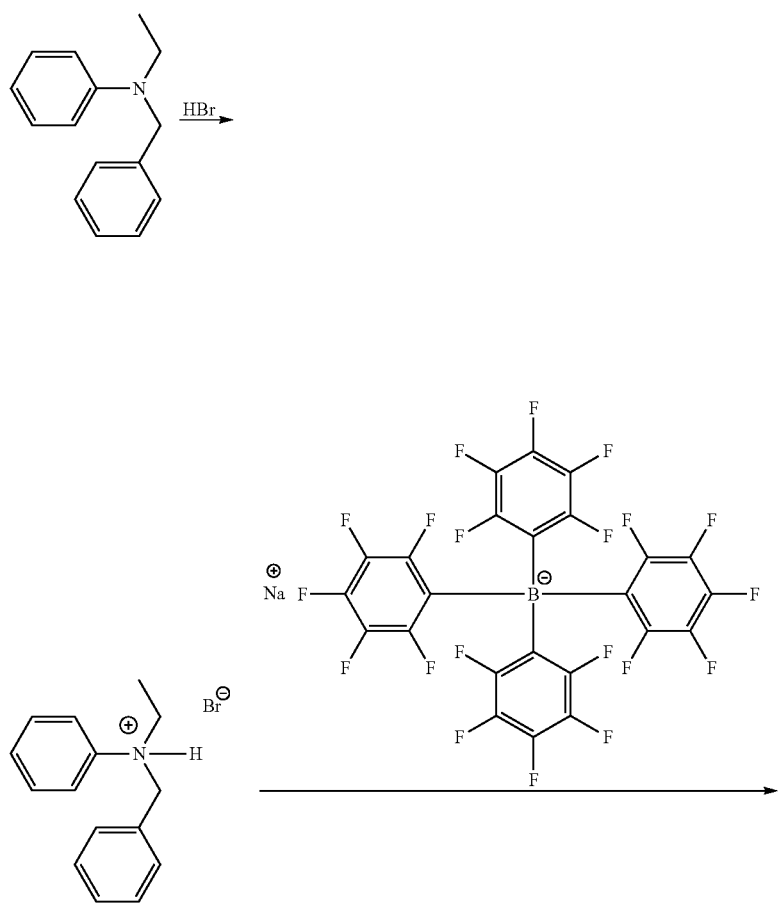

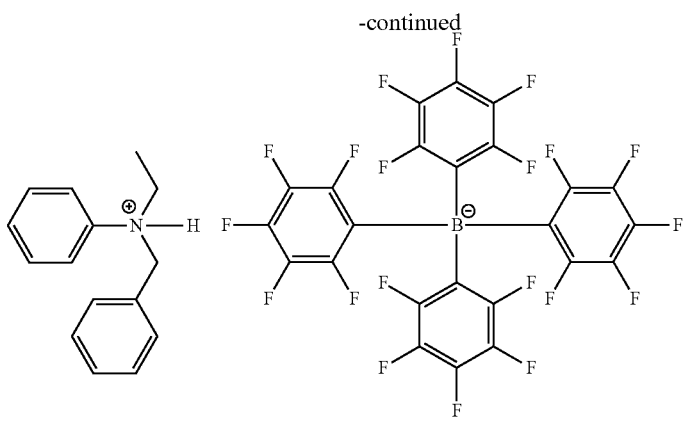

[Synthesis of Ionic Compound 2]

Respective acetone solutions of 0.7 g (0.0024 mol) of N-Benzyl-N-ethylanilinium bomide (II) and 0.66 g (0.0024 mol) of PFBSNA were mixed to produce a white precipitate. This precipitate was separated by filtration (0.39 g), and the solvent was distilled away from the acetone solution to obtain a mixture of an oily matter and a crystal. Toluene was added to this mixture to separate the insoluble matter. The solvent was distilled away from the toluene solution to obtain a light brown oily matter (1.1 g/quantitative). As a result of making an NMR measurement of this oily matter, it was determined that the following ionic compound was produced.

Here is the reaction formula of the reaction mentioned above.

[Chemical Formula 13]

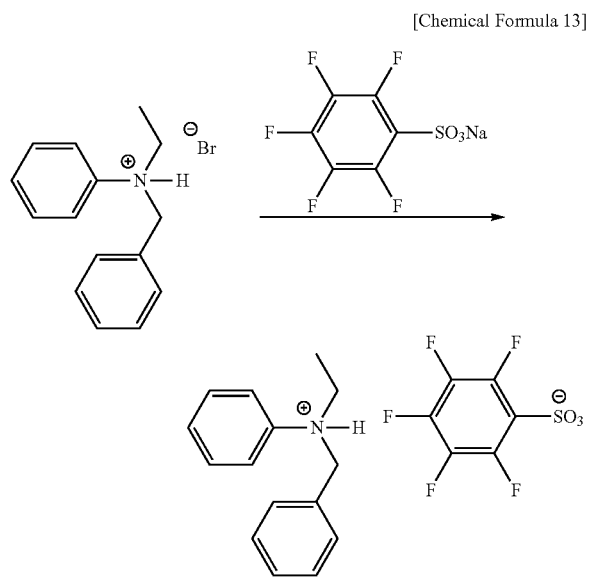

[Synthesis of Ionic Compound 3]

Respective acetone solutions of 0.7 g (0.0024 mol) of N-Benzyl-N-ethylanilinium bomide (II) and 1.3 g (0.0024 mol) of cesium tris(trifuloromethanesulfonyl)methide were mixed and stirred to produce a white precipitate. This precipitate was separated by filtration (0.35 g), and the solvent was distilled away from the acetone solution to obtain a viscous oily matter (left overnight to turn into a mixture of an oily matter and a crystal). To this mixture, a small amount of acetone was added to separate an insoluble matter (this operation was repeated twice). Then, the solvent was distilled away from the acetone solution to obtain a light brown oily matter (15 g/quantitative). As a result of making an NMR measurement of this oily matter, it was determined that the following ionic compound was produced.

Here is the reaction formula of the reaction mentioned above.

[Chemical Formula 14]

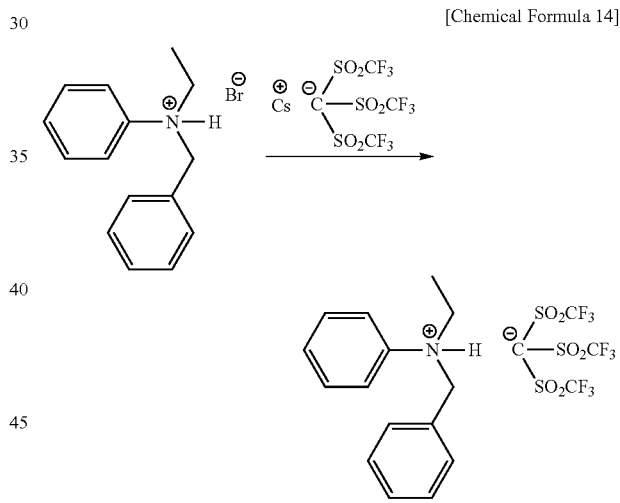

[Synthesis of Ionic Compound 4]

The mixture of 1.7 g of hydrobromic acid (48%) with 2.1 g (0.01 mol) of N,N-Dibutylaniline (I) was slightly heated, shaken up, left for 1 hour, and then subjected to water removal under reduced pressure to achieve crystallization. Checking by proton NMR confirmed the disappearance of N,N-Dibutylaniline (I) and the generation of N,N-Dibutylanilinium bomide (II). Then, 1.43 g (0.005 mol) of (II) mentioned above and 35.1 g (0.005 mol) of sodium tetrakis (pentaphenyl)borate (10% aq.) were mixed and stirred. The mixture was left overnight, and a white precipitate was found in white turbid gel-like matter as a whole. This precipitate was, with the appropriate addition of water thereto, subjected to filtration under reduced pressure, washed with water, and dried to obtain a white solid (yield 3.4 g/reaction yield 77%).

Here is the reaction formula of the reaction mentioned above.

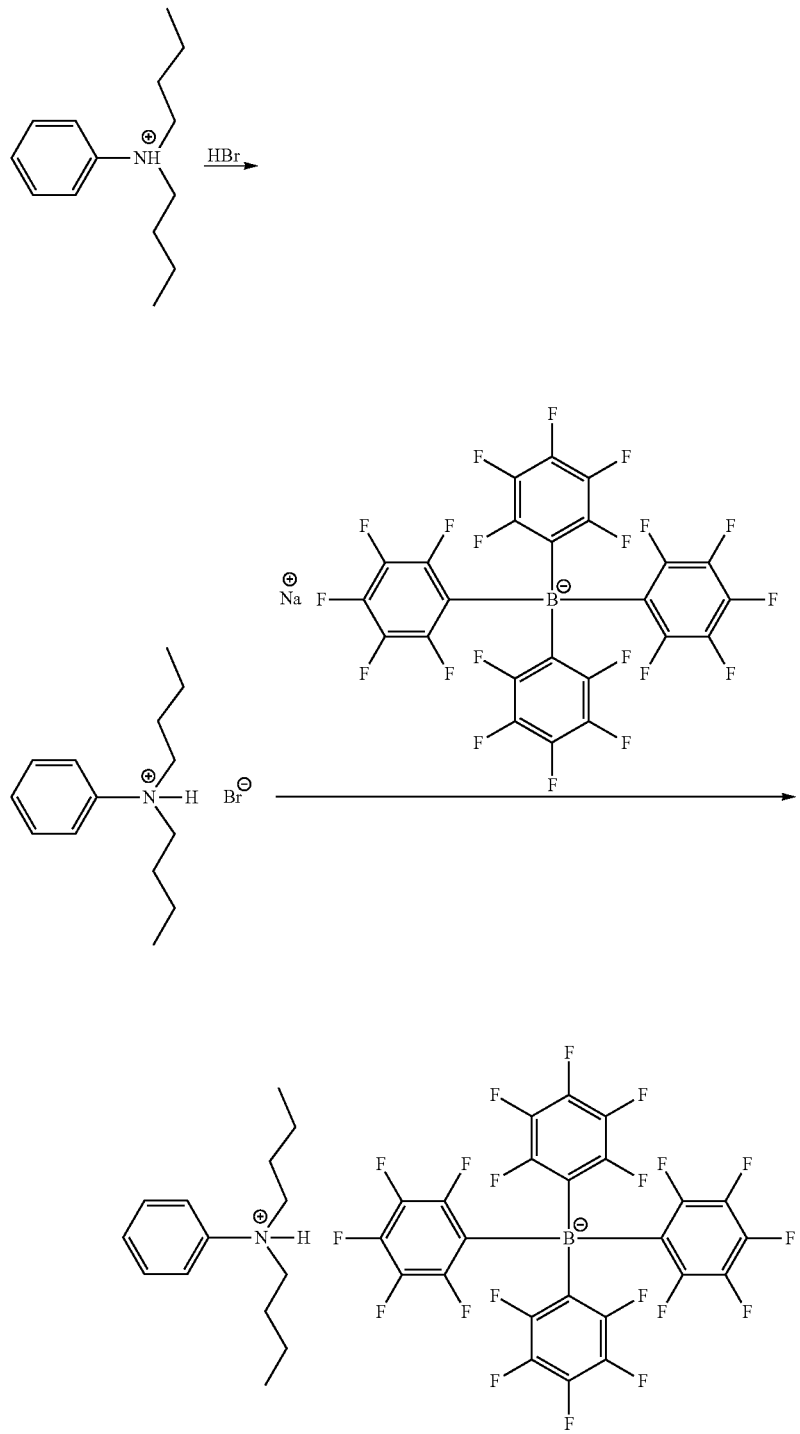

[Chemical Formula 15]

[Synthesis of Ionic Compound 5]

To 1.85 g (6.7 mmol) of N,N-Dibenzylaniline (I) dissolved in 5 mL of acetone, 0.85 g of hydrobromic acid (48%) was added, and shaken up to precipitate a white crystal. The crystal was left overnight, then filtered, washed with acetone, dried to obtain 1.32 g (reaction yield 56%) of white crystal. Checking by proton NMR confirmed the disappearance of N,N-Dibenzylaniline (I) and the generation of N,N-Dibenzylanilinium bomide (II). Then, 1.0 g (2.8 mmol) of (II) mentioned above and 19.9 g (2.8 mmol) of sodium tetrakis(pentaphenyl)borate (10% aq.) were mixed and stirred. The (II) was hardly soluble in water, and thus heated and stirred to separate a white precipitate. Furthermore, the precipitate was subjected ultrasonic agitation, left overnight, filtered, washed with water, and dried to obtain a white solid (yield 2.0 g/reaction yield 76%).

Here is the reaction formula of the reaction mentioned above.

[Chemical Formula 16]

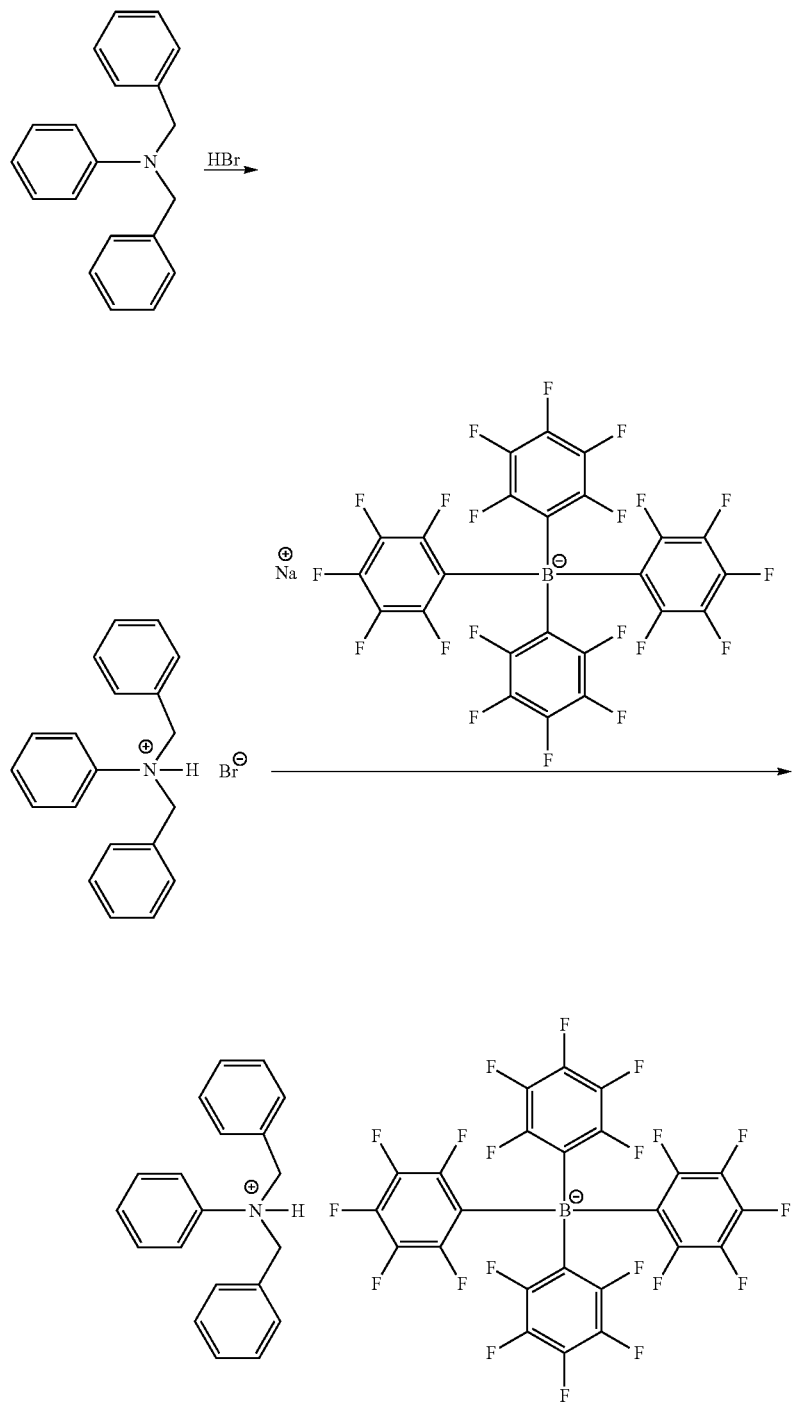

[Synthesis of Ionic Compound 6]

A small amount of acetone was added to a mixture of 2.0 g (0.01 mol) of 4-Octylaniline (I) and 1.7 g of hydrobromic acid (48%) to provide a homogeneous solution. The solution was left overnight, and then subjected to solvent and water removal under reduced pressure to provide a reddish brown viscous oily matter. Checking by proton NMR confirmed the disappearance of 4-Octylaniline (I) and the generation of 4-Octylanilinium bomide (II). Then, 0.95 g (3.3 mmol) of (II) mentioned above and 23.5 g (3.3 mmol) of sodium tetrakis(pentaphenyl)borate (10% aq.) were mixed and stirred. An oily matter was separated by leaving overnight. Toluene was added to this oily matter, and the oily matter was extracted, washed with water, dried to distill away the solvent, and obtain a brown oily matter (yield 2.5 g/reaction yield 84%). As a result of making an NMR measurement of this oily matter, it was determined that the following ionic compound was produced.

Here is the reaction formula of the reaction mentioned above.

[Chemical Formula 17]

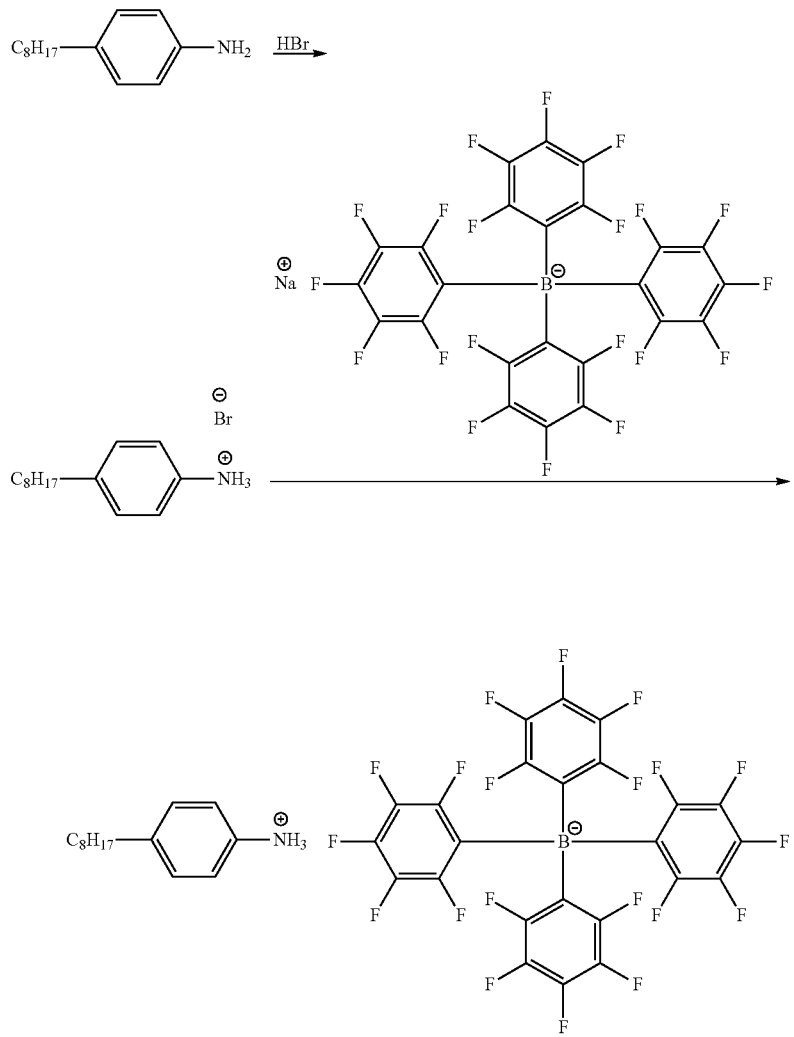

<Synthesis of Charge Transporting Compound>
[Preparation of Pd Catalyst]

In a glove box under a nitrogen atmosphere, under room temperature, tris(dibenzylideneacetone) dipalladium (73.2 mg, 80 μmol) was weighed in a sample tube, and with the addition of anisole (15 ml) thereto, stirred for 30 minutes. Likewise, tris(t-butyl)phosphine (129.6 mg, 640 μmol) was weighed in a sample tube, and with the addition of anisole (5 ml) thereto, stirred for 5 minutes. These solutions were mixed, and stirred at room temperature for 30 minutes to provide a catalyst.

<Synthesis of Charge Transporting Polymer with Cross-Linking Group>

In a three-necked round-bottom flask, the following monomer 1 (4.0 mmol), the following monomer 2 (5.0 mmol), the following monomer 3 (2.0 mmol), and anisole (20 ml) were added, and further added thereto was the prepared Pd catalyst solution (7.5 ml). After stirring for 30 minutes, a solution (20 ml) of 10% tetraethylammonium hydroxide was added. The solvents were all subjected to degassing with nitrogen bubbles for 30 minutes or more, and then used. This mixture was refluxed by heating for 2 hours. These operations were all carried out under a nitrogen stream.

After the completion of the reaction, the organic layer was washed with water, and the organic layer was poured into methanol-water (9:1). The produced precipitate was subjected to suction filtration, and washed with methanol-water (9:1). The obtained precipitate was dissolved in toluene, and reprecipitated from methanol. The obtained precipitate was subjected to suction filtration, dissolved in toluene, and stirred overnight with the addition of triphenylphosphine, polymer-bound on styrene-divinyl benzene copolymer (from Strem Chemicals, Inc., 200 mg with respect to 100 mg of the polymer). After the completion of stirring, the triphenylphosphine, polymer-bound on styrene-divinyl benzene copolymer and the insoluble matter were removed by filtration, and the filtrate was condensed in a rotary evaporator. The residue was dissolved in toluene, and then reprecipitated from methanol-acetone (8:3). The produced precipitate was subjected to suction filtration, and washed with methanol-acetone (8:3). The obtained precipitate was vacuum-dried to obtain the polymer 1. The molecular weight was measured by GPC (polystyrene equivalent) with the use of THF as an eluent. The obtained polymer 1 was 7,800 in number average molecular weight, and 31,000 in weight average molecular weight.

[Chemical Formula 18]

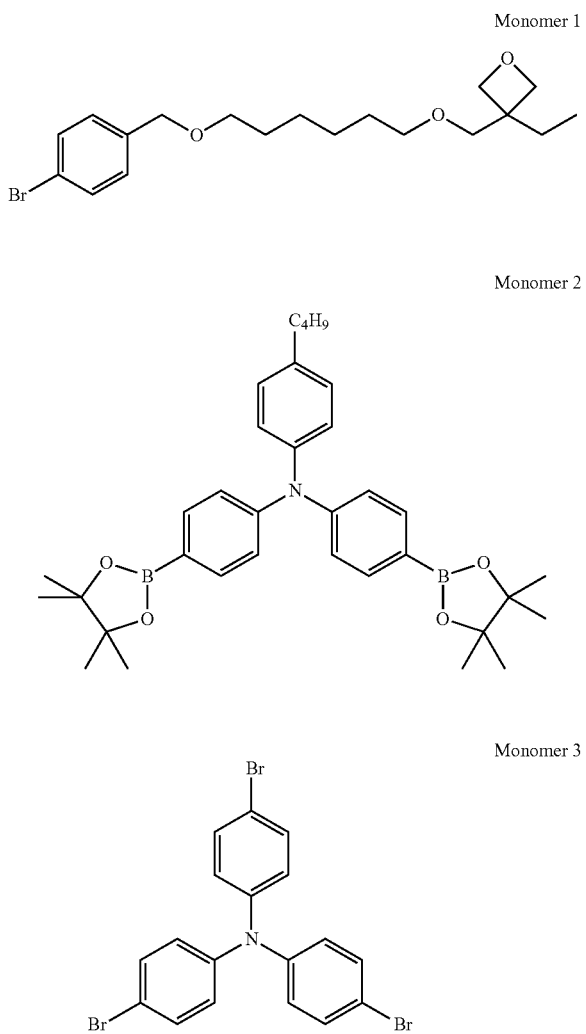

Monomer 1

Monomer 2

Monomer 3

Example 1

Evaluation of Curability

The polymer 1 (5.0 mg) and the ionic compound 1 (0.15 mg) were dissolved in a chlorobenzene solution (1000 µl) to prepare an ink composition. This ink composition was applied onto a quartz plate by spin coating at 3000 rpm. Then, on a hot plate, the composition was heated at 120° C. for 10 minutes to develop a polymerization reaction. After the heating, the quartz plate was immersed in toluene for 1 minute to carry out washing. From the ratio between before and after the washing in the absorbance (Abs) at the absorption maximum (λmax) in UV-vis spectra, the residual film ratio was measured. The measurement result is shown in Table 1.

(Evaluation of Charge Transporting Performance)

For evaluating the charge transporting performance, an evaluation element was prepared as follows.

<Preparation of Charge Transporting Performance Evaluation Element>

Onto a glass substrate of 1.6 mm in width, obtained by ITO patterning, a mixed solution of the polymer 1 (100 mg), the ionic compounds 1 to 6 (3.0 mg), and anisole (1.91 mL) were applied by spin coating at 3000 min$^{-1}$, and heated at 120° C. for 10 minutes on a hot plate to prepare a charge transporting film (150 nm). Next, the obtained glass substrate was transferred into a vacuum deposition machine for vapor deposition of aluminum (100 nm in film thickness).

After the vapor deposition of aluminum, the substrate was transferred into a dry nitrogen atmosphere without being opened to the atmosphere, and sealing was carried out by attaching sealing glass of 0.7 mm alkali-free glass subjected to spot facing at 0.4 mm and the ITO substrate to each other with the use of a light curable epoxy resin, thereby preparing a charge transporting performance evaluation element.

With the ITO of the charge transporting performance evaluation element as a positive electrode and the aluminum thereof as an anode, a voltage was applied. The applied voltage in the case of applying a current at 50 mA/cm$^2$ is shown in Table 1.

Examples 2 to 6

Except that the ionic compound 1 in Example 1 was changed to the ionic compounds 2 to 6, ink compositions were prepared in the same way as in Example 1 to evaluate the curability and charge transporting performance. The evaluation results are shown in Table 1.

Comparative Example 1

Except that the ionic compound 1 in Example 1 was changed to the following ionic compound, an ink composition was prepared in the same way as in Example 1 to evaluate the curability and charge transporting performance. The evaluation results are shown in Table 1.

[Chemical Formula 19]

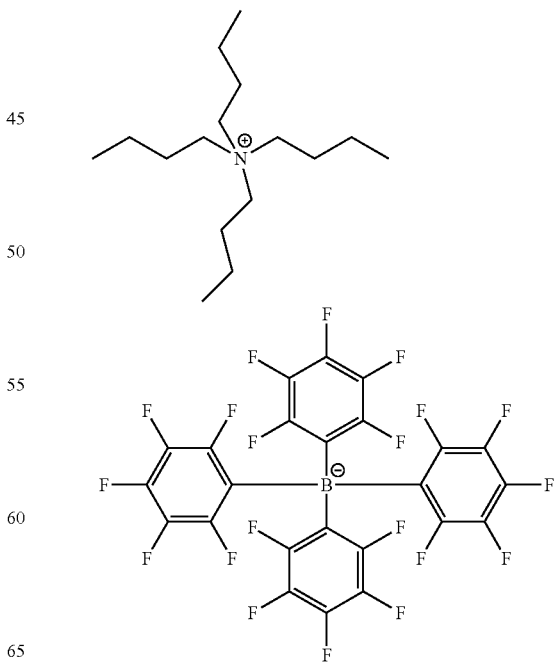

TABLE 1

| | Ionic Compound | Curability Residual Film Ratio (%) | Electron Transporting Performance Applied Voltage (V) |
|---|---|---|---|
| Example 1 | Ionic Compound 1 | 99.2 | 1.4 |
| Example 2 | Ionic Compound 2 | 97.2 | 2.9 |
| Example 3 | Ionic Compound 3 | 98.9 | 3.1 |
| Example 4 | Ionic Compound 4 | 99.1 | 1.6 |
| Example 5 | Ionic Compound 5 | 99.8 | 1.5 |
| Example 6 | Ionic Compound 6 | 99.8 | 1.4 |
| Comparative Example 1 | Quaternary Ammonium | 23 | 6.6 |

From Table 1, it is determined that favorable results have been achieved for both the curability and charge transporting performance at the same time in Examples 1 to 6, as compared with Comparative Example 1.

More specifically, Examples 1 to 6 have succeeded in developing sufficient resistance to solvents for the deposited layers, in spite of curing at the low temperature of 120° C.

In addition, the organic electronic material according to the present invention, which allows hole current to flow easily, is considered to make a contribution to reduction in voltage for organic electronic elements.

Example 7

Preparation of Organic EL Element

Onto a glass substrate of 1.6 mm in width, obtained by ITO patterning, an application solution obtained by mixing the polymer 1 (10 mg) obtained above, the ionic compound 1 (0.3 g), and chlorobenzene (1000 μl) was applied by spin coating at 3000 min$^{-1}$, and then cured by heating at 120° C. for 10 minutes on a hot plate to form a hole injecting layer (30 nm).

Next, the obtained glass substrate was transferred into a vacuum deposition machine for vapor deposition of αNPD (40 nm), (αNPD+Ir(piq)$_3$ (5:1, 20 nm), BAlq (10 nm), Alq$_3$ (40 nm), LiF (0.5 nm in film thickness), and Al (100 nm in film thickness) in this order.

After the formation of the electrode, the substrate was transferred into a dry nitrogen atmosphere without being opened to the atmosphere, and sealing was carried out by attaching sealing glass of 0.7 mm alkali-free glass subjected to spot facing at 0.4 mm and the ITO substrate to each other with the use of a light curable epoxy resin, thereby preparing a high-molecular type organic EL element of multi-layer structure. Subsequent experiments were made at room temperature (25° C.) in the atmosphere. When a voltage was applied with the ITO of the organic EL element as a positive electrode and the Al thereof as a cathode, a red light emission was observed at 3.8 V, and the current efficiency at a luminance of 1000 cd/m$^2$ was 1.8 cd/A. It is to be noted that current-voltage characteristics were measured with microammeter 4140B from Hewlett-Packard Company, whereas the luminance was measured with the use of a luminance meter Pritchard 1980B from Photo Research, Inc.

Furthermore, as lifetime characteristics, the luminance was measured with BM-7 from Topcon Corporation while applying a constant current, to measure the half-life of the luminance from the initial luminance (3000 cd/m$^2$), which was 500 hours.

Comparative Example 2

Except that the ionic compound 1 was changed to the ionic compound used in Comparative Example 1, an organic EL element was prepared in the same way as in Example 7. A red light emission was observed at 6.0 V, and the current efficiency at a luminance of 1000 cd/m$^2$ was 1.2 cd/A. Furthermore, as lifetime characteristics, the luminance was measured with BM-7 from Topcon Corporation while applying a constant current, to measure the half-life of the luminance from the initial luminance (3000 cd/m$^2$), which was 10 hours.

From the comparison between Example 7 and Comparative Example 2 described above, it is determined that the organic electronic material according to the present invention is also excellent in lifetime characteristics.

REFERENCE SIGNS LIST 1 light emitting layer
2 anode
3 hole injecting layer
4 cathode
5 electron injecting layer
6 hole transporting layer
7 electron transporting layer
8 substrate

The invention claimed is:

1. An organic electronic material comprising at least an ionic compound represented by the following general formula (1), and a charge transporting compound including a charge transporting unit:

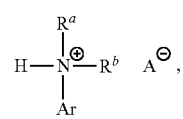

General Formula (1)

in the general formula (1), Ar represents an aryl group or a heteroaryl group, $R^a$ to $R^b$ each independently represent a hydrogen atom (H), an alkyl group, a benzyl group, an aryl group, or a heteroaryl group, Ar, $R^a$ and $R^b$ may be linked to each other to form a ring, at least one of $R^a$ to $R^b$ is any of a hydrogen atom (H), an alkyl group, and a benzyl group, and A represents an anion, wherein the anion is represented by the following formulas (1b) to (5b):

(1b)

(2b)

(3b)

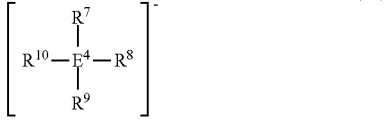

(4b)

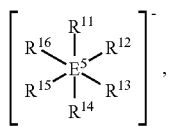

in the general formulas (1b) to (5b), $Y^1$ to $Y^6$ each independently represent a divalent linking group; $R^1$ to $R^{16}$ each independently represent an electron attractive organic substituent, $R^1$ to $R^{16}$ may further have substituents and hetero atoms therein, and $R^2$ and $R^3$, $R^4$ to $R^6$, $R^7$ to $R^{10}$, or $R^{11}$ to $R^{16}$ may be each linked to form a ring or a polymer; and $E^1$, $E^2$, $E^3$, $E^4$, and $E^5$ respectively represent an oxygen atom, a nitrogen atom, a carbon atom, a boron atom or a gallium atom, and a phosphorus atom or an antimony atom.

2. The organic electronic material according to claim 1, wherein at least one of $R^a$ to $R^b$ is any of a hydrogen atom (H), an alkyl group having two or more carbon atoms, and a benzyl group, provided that in a case where one of $R^a$ or $R^b$ is a hydrogen atom (H), the other of $R^a$ or $R^b$ is a hydrogen atom (H).

3. The organic electronic material according to claim 1, wherein the charge transporting compound is an aromatic amine, a carbazole, or a thiophene.

4. The organic electronic material according to claim 1, wherein the charge transporting compound is a polymer or an oligomer.

5. The organic electronic material according to claim 1, wherein the charge transporting compound comprises one or more polymerizable substituents.

6. The organic electronic material according to claim 5, wherein the polymerizable substituents are any of an oxetane group, an epoxy group, and a vinyl ether group.

7. An ink composition comprising the organic electronic material according to claim 1, and a solvent.

8. An organic electronic element including a layer formed by applying the organic electronic material according to claim 1 on a substrate.

9. The organic electronic element according to claim 8, wherein the layer formed has been polymerized for insolubilization.

10. The organic electronic element according to claim 9, wherein another layer is further formed on the insolubilized layer to provide a multi-layer.

11. The organic electronic element according to claim 8, wherein the substrate is a resin film.

12. An organic electronic element including a layer formed by applying the ink composition according to claim 7 on a substrate.

13. The organic electronic element according to claim 12, wherein the substrate is a resin film.

14. The organic electronic material according to claim 1, wherein Ar represents a substituted or unsubstituted phenyl group, a substituted or unsubstituted C1 to C12 alkoxyphenyl group, or a substituted or unsubstituted C1 to C12 alkylphenyl group.

15. The organic electronic material according to claim 14, wherein the charge transporting compound is a polymer or an oligomer.

16. The organic electronic material according to claim 14, wherein the charge transporting compound comprises one or more polymerizable substituents.

17. An ink composition comprising the organic electronic material according to claim 14, and a solvent.

18. The organic electronic material according to claim 1, wherein the ionic compound is represented by the following formula:

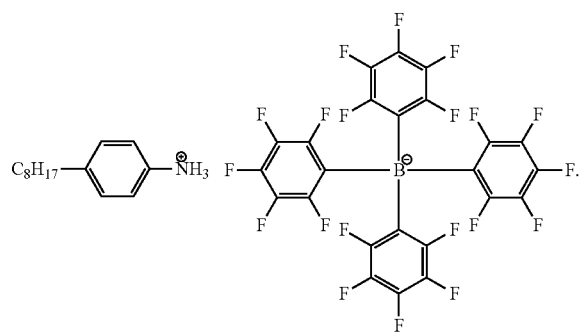

19. The organic electronic material according to claim 14, wherein the charge transporting compound is an aromatic amine, a carbazole, or a thiophene.

20. The organic electronic material according to claim 1, wherein Ar represents a substituted or unsubstituted 1-naphthyl group, a substituted or unsubstituted 2-naphthyl group, a substituted or unsubstituted 1-anthracenyl group, a substituted or unsubstituted 2-anthracenyl group, a substituted or unsubstituted 9-anthracenyl group, a substituted or unsubstituted phenanthrene-yl group, a substituted or unsubstituted pyrene-yl group, or a substituted or unsubstituted perylene-yl group.

* * * * *